(12) United States Patent
Wang et al.

(10) Patent No.: US 6,852,889 B2
(45) Date of Patent: Feb. 8, 2005

(54) ANTIOXIDANT NITROXIDES AND NITRONES AS THERAPEUTIC AGENTS

(75) Inventors: Yuqiang Wang, Cupertino, CA (US); James W. Larrick, Woodside, CA (US)

(73) Assignees: Panorama Research, Inc., Mountain View, CA (US); NeuroMolecular, Inc., Emoryville, CA (US)

( * ) Notice: Subject to any disclaimer, the term of this patent is extended or adjusted under 35 U.S.C. 154(b) by 0 days.

(21) Appl. No.: 10/769,128

(22) Filed: Jan. 30, 2004

(65) Prior Publication Data

US 2004/0186320 A1 Sep. 23, 2004

Related U.S. Application Data

(63) Continuation of application No. 10/114,200, filed on Apr. 2, 2002, now Pat. No. 6,717,012.
(60) Provisional application No. 60/280,097, filed on Apr. 2, 2001.

(51) Int. Cl.⁷ .......................... A61K 31/13; A01N 33/02
(52) U.S. Cl. ...................................... 564/265; 514/638
(58) Field of Search ........................... 564/265; 514/638

(56) References Cited

U.S. PATENT DOCUMENTS

| | | | |
|---|---|---|---|
| 4,904,681 A | | 2/1990 | Cordi et al. |
| 5,061,721 A | | 10/1991 | Cordi et al. |
| 5,086,072 A | | 2/1992 | Trullas et al. |
| 6,046,232 A | * | 4/2000 | Kelleher et al. ............ 514/464 |

FOREIGN PATENT DOCUMENTS

WO     99/20601    *   4/1999    ......... C07C/291/02

OTHER PUBLICATIONS

Murray et al, J. Org. Chem., 1990, 55, 2954–2957.*
Barth, et al. (1996). *Exp. Neurol.* 141: 330–336.
Bhat, et al. (1995). *Neuroendocrinology* 62 (2) 178–186.
Bliss, et al. (1993). *Nature* 361:31–39.
Bormann (1989). *Eur. J. Pharmacol.* 166: 591–592.
Bredt, et al. (1990). *Nature* 347: 768–770.
Chamulitrat, et al. (1993). *J. Biol. Chem.* 268: 11520–11527.
Chen, et al. (1992). *J. Neurosci.* 12: 4427–4436.
Cohan, et al. (1987). *J. Neurosci.* 7: 3588–3599.
Connor, et al. (1987). *J. Neurosci.* 7: 1384–1400.
Connor, et al. (1988). *Science* 240: 649–653.
Culter (1991). *Ann. New York Acad. Sci.* 621: 1–28.
Deyer, et al. (1990). *Science* 248: 364–367.
Edamatsu, et al. (1995). *Biochem. Biophys. Res. Commun.* 211: 847–849.
Foster, et al. (1987). *Nature* 329: 395–396.
Garthwaite, et al. (1968). *Nature* 336: 385–388.
Gelvan, et al. (1991). *Proc. Natl. Acad. Sci. USA* 88: 4680–4684.

(List continued on next page.)

Primary Examiner—Brian Davis
(74) Attorney, Agent, or Firm—Ivor R. Elrifi; Mintz Levin Cohn Ferris Glovsky & Popeo, PC

(57) ABSTRACT

The invention provides novel adamantane compounds having one of the following formulas:

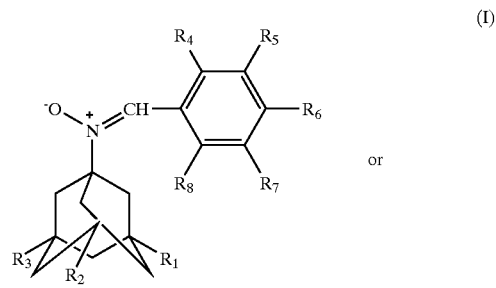

(I)

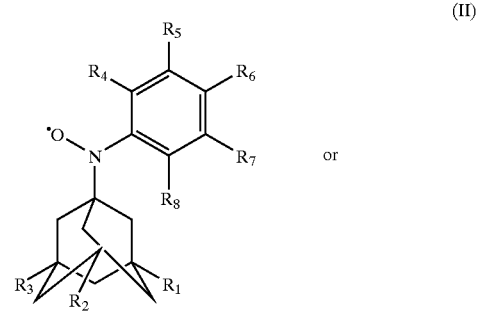

(II)

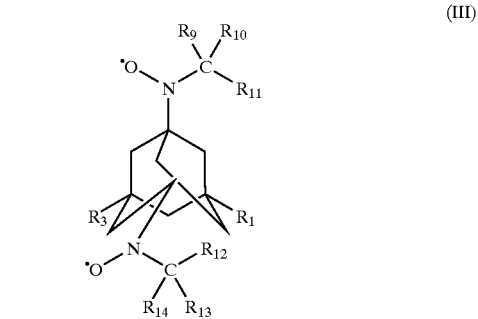

(III)

wherein:
$R_1$ and $R_3$ are H, OH, alkyl, cycloalkyl, amino or aryl, and can be the same or different;
$R_2$ is H, $NH_2$, alkyl, OH, COOH, amino, amide, or carbamate;
$R_4$–$R_8$ are H, OH, $NH_2$, alkyl, OH, COOH, ester, amino, amide, or alkyloxy, and can be the same or different;
$R_9$–$R_{14}$ are H, alkyl, or phenyl, and can be the same or different;
and wherein when any of $R_1$–$R_8$ is amino, the compounds are the free bases and their acid addition salts.

The present invention also relates to compositions and methods for treating and/or preventing neurological and inflammatory disorders in a patient by administering a therapeutically effective amount of the compounds of formula (I), (II) or (III) and a pharmaceutically acceptable carrier.

14 Claims, 3 Drawing Sheets

OTHER PUBLICATIONS

Görtelmeyer, et al. (1992). *Arznheim–Forsch/Drug Res. 42*: 904–913.
Graham, et al. (1997). *JAMA 277*: 1775–1781.
Grynkiewicz, et al. (1985). *J. Biol. Chem. 260*: 3440–3450.
Hahn, et al. (1988). *Proc. Natl. Acad. Sci. USA 85*: 6556–6560.
Janzen, et al. (1992). *Free Rad. Biol. Med. 12*: 169–173.
Johnson, et al. (1990). *Annu Rev. Pharmacol. Toxicol. 30*: 707–750.
Keilhoff, et al. (1992). *Eur. J. Pharmacol. 219*: 451–454.
Klockgether and Turski (1989). *Trends Neurosci. 12*: 285–286.
Klockgether and Turski (1990). *Ann. Neurol. 28*: 539–546.
Kornhuber, et al. (1989). *Eur. J. Pharmacol. 166*: 589–590.
Kornhuber, et al. (1991). *Eur. J. Pharmacol. (Mod. Pharmacol. Sect.) 206*: 297–300.
Kornhuber, et al. (1994). *J. Neural Transm. Suppl. 43*: 91–104.
Kotake and Janzen (1991). *J. Am. Chem. Soc. 113*: 9503–9506.
Krishna, et al. (1996). *J. Biol. Chem. 271*: 26018–26025.
Krishna, et al. (1996). *J. Biol Chem. 271*: 26026–26031.
Levy, et al. (1990). *Neurology 40*: 852–855.
Levy, et al. (1990). *Neurosci. Lett. 110*: 291–296.
Masou, et al. (1986). *Eur. J. Pharmacol. 130*: 187–195.
Mattson, et al. (1989). *J. Neurosci. 9*: 3728–3740.
Mayer, et al. (1990). *Trends Pharmacol. Sci. 11*: 254–260.
McCully (1969). *Am. J. Pathol. 56*: 111–128.
McDonald and Johnston (1990). *Brain Res. Rev. 15*: 41–70.
Mohsen, et al. (1995). *Mol. Cell. Biochem. 145*: 103–110.
Nygard, et al. (1997). *N. Engl. J. Med. 337*: 230–236.
Rabey, et al. (1992). *J. Neural Transm. 4*: 277–282.
Reiser, et al. (1988). *Brain Res. 443*: 338–344.
Riederer, et al. (1991). *Lancet 338*(8773): 1022–1023.
Sack, et al. (1996). *Neurosci. Lett. 205*: 181–184.
Samuni, et al. (1988). *J. Biol. Chem. 263*: 17921–17924.
Schmidt, et al. (1990). *Trends Neurosci. 13*: 46–47.
Schwab, et al. (1969). *J. Am. Med. Assoc. 208*: 1168–1170.
Smith, et al. (1984). *ACTA Neurol. Scand. 69*: 385–401.
Tal (1996). *Neuroreport 7*: 1382–1384.
Upchurch, et al. (1997). *J. Biol. Chem. 272*: 17012–17017.
Walder, et al. (2000). *Biol. Psychiatry 48*: 1121–1132.
Williams, et al. (1985). *Nature 318*: 558–561.
Ziemann, et al. (1998). *Electroencephalogr Clin Neurophysiol 109*(4):321–330.
Choi (1988). *Neuron 1*: 623–634.
Maj (1982). *Arzneim–Forsch/ Drug Res 32*: 1256–1259.
Sviridov, et al. (1989) "C–hydroxylation of N–adamantylanilines with hexafluoroacetone and methyl trifluoropyruvate." Izv. Akad. Nauk SSSR, Ser. Khim. 10:2348–50 (abstract only).

* cited by examiner (I)  or  (II)  or  (III)

Clinical Studies with Memantine

Abbreviations: C-O = cross-over; O = open-label; IV = intravenous; P-C = placebo-controlled; PBO = placebo; PO = oral; R = randomized; wks = weeks

| Study | Study Design/N | Dose/Duration study | Efficacy | Adverse Events |
|---|---|---|---|---|
| Parkinson's disease | | | | |
| Fischer et al. 1977 | O/12 | IV, 40 mg in 2 hours single dose | + motor drive and rigor | Dizziness, fatigue, lack of coordination sense of well-being at 6 hours post-infusion |
| Rabey et al. 1992 | O/12 | PO, 10-30 mg/day X 4 wks | + Parkinson's syndrome in 5/10 | Nausea, abdominal pain, confusion and dizziness, psychomotor agitation |
| Riederer et al. 1991 | O/4 | PO, 10-30 mg/day X 6 wks | 1 memantine pt had mild improvement in motor symptoms | Psychosis in 2 patients (concomitant Meds included L-dopa, amantadine) |
| Schneider et al. 1984 | R, DB, P-C/67 | PO, 30 mg/day X 6 wks | Significant improvement in fine motor ability in memantine group | 90% tolerated well |
| Merello et al. 1999 | R, DB, CO, P-C/12 | PO, 30 mg/day X 2 wks | Improvement in Parkinsonian Symptoms | Mild transient drowsiness and nausea |
| Dementia | | | | |
| Fleishchhacker et al. 1986 | R, SB, P-C/20 | IV, 20-30 mg/day X 5 wks | 5 Memantine and 4 PBO pts improved enough for discharge | Delusions of guilt, delirium, mild hypotonia |
| Ditzler 1991 | R, DB, P-C/66 | PO, 10-30 mg/day X 6 wks | Memantine > PBO | Agitation, increased motor activity, insomnia, restlessness |
| Görtelmeyer and Erbler 1992 | R, DB, P-C/88 | PO, 10-20 mg/day X 6 wks | Memantine > PBO | Akathisia, increased motor activity, Insomnia, headache |
| Pantev et al. 1993 | R, DB, P-C/60 | PO, 10-30 mg/day X 4 wks | Memantine > PBO | Restlessness, akathisia, vertigo |
| Rieke and Glaser 1996 | O/1420 | PO, 13-26 mg/day | Memantine end > baseline | Restlessness, nausea, fatigue |
| Neurogenic bladder | | | | |
| Grossman and Schütz 1982 | O/18 | PO, 20-70 mg/day X 2 wks | Improvement in bladder function | Agitation, giddiness, impaired Concentration and sleep |
| Spasticity | | | | |
| Mundinger and Milics 1985 | O/37 | PO, 30-60 mg/day X 8 wks | Improvement in neurological symptoms | 78% tolerated well; some patients giddiness, nausea, stupor |
| Rohde 1982 | O/30 | IV, 10-30 mg/day/4-14 months | Improvement in spasticity 17/30 | Fatigue, increased transaminases, GGT |
| Bayerl and Gruia 1985 | Single blind/ Cross-over/30 | PO, 20-30 mg/day X 6 wks | 61% improved | Mood elevation, increase in drive |
| Leakow 1987 | O/226 | PO, 10-30 mg/day X 6 wks | Improvement in fine motor movement, muscle tone | Dizziness, tiredness, headaches |
| Craniocerebral trauma | | | | |
| Milmer 1982 | O/45 | IV, 60-80 mg/day X 10 days | Improvement in level of consciousness | Well-tolerated |
| Chronic CNS Disease | | | | |
| Ambrozi and Danielczyk 1988 | DB, P-C/30 | ? Dose X 6 weeks | Memantine > PBO | Euphoria, vertigo |
| Neuropathic pain | | | | |
| Nikolajsen et al. 2000 | R, DB, C-O, P-C | PO, 5-20 mg/day X 6 wks | Memantine + PBO | Nausea, headache, skin rash |

FIG. 2

ANTIOXIDANT NITROXIDES AND NITRONES AS THERAPEUTIC AGENTS

RELATED APPLICATION

The present application is a continuation of Ser. No. 10/114,200, filed Apr. 2, 2002 now U.S. Pat. No. 6,717,012, which claims the benefit, under 35 U.S.C. §120, of U.S. Provisional Patent Application Ser. No. 60/280,097, which was filed on Apr. 2, 2001.

FIELD OF THE INVENTION

The present invention relates to novel compounds, compositions, and methods for the treatment and/or prevention of neurological, inflammatory, neuropsychiatric and aging-related disorders that result primarily from the overproduction of nitric oxide and other free radicals.

BACKGROUND OF THE INVENTION

Oxygen is vital to most human and animal life. It can, however, give rise to a variety of reactive oxygen species ("ROS") as part of normal metabolism. Reactive species are produced by the body under normal conditions, and indeed are part of normal metabolism. The body is equipped with a variety of mechanisms which render ROS inactive.

Under normal conditions, the rate of ROS production does not exceed the capacity of the tissue to catabolize them. However, under certain conditions, ROS levels are raised beyond the capacity of these protective mechanisms (e.g., irradiation, environmental factors, iron loading, etc.) or when these mechanisms are faulty (e.g., genetic defects), and the ROS can cause cellular and tissue damage leading to a variety of diseases and even death. Proteins, lipids, and DNA are all substrates for ROS attack. It has been calculated that for every 100 tons of oxygen consumed two tons form reactive oxygen species. For every $10^{12}$ oxygen molecules entering a cell each day $\frac{1}{100}$ damages protein and $\frac{1}{200}$ damages DNA. It is this damage to DNA, proteins, and lipids that makes the reactive oxygen species so dangerous, especially when the body's natural defenses are compromised.

Increasing evidence suggests that oxidative stress plays an important role in aging. The level of some antioxidant enzymes such as sodium oxide dismutase (SOD) and anti-oxidants such as uric acid, beta-carotene and vitamin E have a positive correlation with the life-span of species. Namely, the level decreases from human to chimpanzee to mouse (Culter, *Free Radicals in Biology*, vol. 4: p. 371, 1984). One hypothesis is that cells are damaged by free radicals and the damaged cells cannot function properly. The accumulation of damages to cells leads to aging (Culter, Id.). Another hypothesis is that free radicals cause cells to dysdifferentiate from their proper state of differentiation. This dysdifferentiation of cells leads to aging and all kinds of age-related diseases. (Culter, Id.). In spite of the disagreement on the mechanism of aging by those skilled in the art, it is clear that free radicals cause aging and age-related diseases. Free radicals have been implicated in stroke, ischemia-reperfusion, cardiovascular diseases, carcingogenesis and neurological diseases, including Alzheimer's disease, Parkinson's disease, dementia and Hodgkin's disease.

Complications of atherosclerosis, such as myocardial infarction, stroke and peripheral vascular disease account for half of the deaths in the United States. Arteriosclerosis begins with an injury to the endothelial cells and is associated with the proliferation of muscle cells inside the arteries. In the process of atherosclerosis, blood becomes thick and platelets, oxidized low density lipoprotein (LDL, the major lipid in LDL is cholesterol esters) and other substances begin to adhere to the walls of the arteries causing the formation of plaque. The oxidation of LDL is caused by free radicals. It was first recognized in 1969 (McCully, *Amer. J. Pathol.* 56:111, 1969), and only recently rediscovered, that high level of plasma homocysteine is associated with an increased rate of death due to coronary artery disease (Nygard et al., *N. Engl. J. Med.* 24: 337, 1997; Graham et al., *JAMA* 277:1775, 1997). Homocysteine injures endothelial cells, thereby causing atherosclerosis through a number of mechanisms, including the generation of hydrogen peroxide ($H_2O_2$). It has been reported that homocysteine decreased the bioavailability of NO (not its production) and impaired the intracellular antioxidant enzymes, especially the glutathione peroxidases (Upchurch et al., *J. Biol. Chem.* 272: 17012, 1997). The key event in the process is generation and presence of free radicals. The increase of hydrogen peroxide ($H_2O_2$) can be a cause or a result. Homocysteine causes the production free radicals including superoxide ($O_2^{•-}$) which reacts with NO causing its decreased bioavailability and the production of hydroxyl radical (•OH), or undergoes dismutation by SOD to produce hydrogen peroxide ($H_2O_2$). Hydrogen peroxide ($H_2O_2$) is further converted to the reactive hydroxyl radical (•OH) through the Fenton reaction and the metal-catalyzed Haber-Weiss reaction. The free radicals produced as a result of these reactions will damage the antioxidant enzymes which prevents the detoxification of free radicals. It is clear that scavenging free radicals will prevent the toxic effects of LDL and homocysteine and results in the prevention of atherosclerosis.

Extensive research efforts have been made to counter the damaging effects caused by free radicals which includes the use of antioxidant enzymes and antioxidants. Unfortunately, protein enzymes are too big to penetrate the cell wall and blood brain barrier. Antioxidants alone are not satisfactory for various reasons including the fact that they are consumed by free radicals and, thus, a large quantity is needed.

Several reactive oxygen species exist. Diatomic molecular oxygen ($O_2$) readily reacts to form partially reduced species, which are generally short-lived and highly reactive and include the superoxide anion ($O_2^{•-}$) a free radical), hydrogen peroxide $H_2O_2$ and the hydroxyl radicals (•OH).

The ROS are the byproducts of mitochondrial electron transport, various oxygen-utilizing enzyme systems, peroxisomes, and other processes associated with normal aerobic metabolism as well as lipid peroxidation. These damaging byproducts further react with each other or other chemicals to generate more toxic products. For example, hydrogen peroxide $H_2O_2$ can be transformed to the highly reactive hydroxyl radical (•OH) through the Fenton reaction and the metal catalyzed Haber-Weiss reaction:

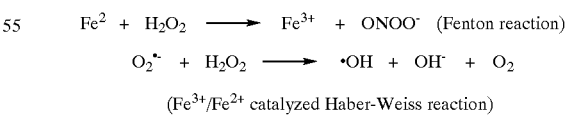

($Fe^{3+}/Fe^{2+}$ catalyzed Haber-Weiss reaction)

Superoxide ($O_2^{•-}$) reacts with nitric oxide (NO) to form the toxic peroxynitrite ($ONOO^-$) which further decomposes to release the hydroxyl radical (•OH).

Human beings have a defense system against toxic byproducts of metabolism including enzymes such as superoxide dismutase ("SOD"), catalases, peroxidases and antioxidants such as vitamins (e.g., vitamin A, beta-carotene, vitamin C and vitamin E), glutathione, uric acid and other phenolic compounds. SOD catalyzes the conversion of superoxide ($O_2^{\cdot-}$) into hydrogen peroxide ($H_2O_2$) and oxygen ($O_2$).

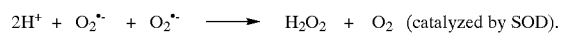

Hydrogen peroxide ($H_2O_2$) can be transformed by catalases and peroxidases to oxygen ($O_2$) and water.

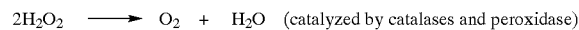

Despite the high efficiency of the defense system, some of these damaging species escape. The escaped reactive oxygen species and their products react with cellular DNA, protein and lipid resulting in DNA damage and peroxidation of membrane lipids. The deleterious results caused by reactive oxygen species are termed oxidative stress which affects normal gene expression, cell differentiation (Culter, *Free Radicals in Biology*, vol. 4, p.371, 1984; Culter, *Ann. New York Acad. Sci.* 621: 1, 1991) and leads to cell death. Oxidative stress is now considered to be responsible for many health problems like cardiovascular and neurological diseases, cancer and other aging-related diseases as well as the human aging process.

Receptors to the neuroexcitatory amino acid, glutamate, particularly the N-methyl-D-aspartate (NMDA) subtype of these receptors, play critical roles in the development, function and death of neurons (see, Mc Donald J W et al., *Brain Research Reviews*, 15: 41–70 (1990) and Choi W, *Neuron*, 1: 623–34 (1988) incorporated herein by reference). The N-methyl-D-aspartate (NMDA) receptor is a postsynaptic, ionotropic receptor which is responsive to, inter alia, the excitatory amino acids glutamate and glycine and the synthetic compound NMDA, hence the receptor name. The NMDA receptor controls the flow of both divalent ($Ca^{2+}$) and monovalent ($Na^+$ and $K^+$) ions into the postsynaptic neuronal cell through a receptor associated channel (see, Foster et al., *Nature*, 329: 395–396 (1987); Mayer et al., *Trends in Pharmacol. Sci.*, 11: 254–260 (1990) incorporated herein by reference).

The NMDA receptor has been implicated during development in specifying neuronal architecture and synaptic connectivity, and may be involved in experience dependent synaptic modifications. In addition, NMDA receptors are also thought to be involved in long-term potentiation, central nervous system (CNS) plasticity, cognitive processes, memory acquisition, retention, and learning. Furthermore, the NMDA receptor has also drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptor which opens the ligand-gated ion channel thereby allowing $Ca^{2+}$ influx producing a high level of intracellular $Ca^{2+}$ which activates biochemical cascades resulting in protein, DNA, and membrane degradation leading to cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Blockage of the NMDA receptor $Ca^{2+}$ channel by the animal anesthetic PCP (phencyclidine) produces a psychotic state in humans similar to schizophrenia (reviewed in Johnson et al., *Annu. Rev. Pharmacol. Toxicol.*, 30: 707–750 (1990) incorporated herein by reference). Further, NMDA receptors have also been implicated in certain types of spatial learning, (see, Bliss et al., *Nature*, 361: 31 (1993), incorporated herein by reference). Interestingly, both the spatial and temporal distribution of NMDA receptors in mammalian nervous systems have been found to vary. Thus, cells may produce NMDA receptors at different times in their life cycles and not all neural cells may utilize the NMDA receptor.

Due to its broad-spectrum of neurological involvement, yet non-universal distribution, investigators have been interested in the identification and development of drugs capable of acting on the NMDA receptor. Drugs that can modulate the NMDA receptor are expected to have enormous therapeutic potential. For instance, U.S. Pat. No. 4,904,681, issued to Cordi et al., and incorporated herein by reference, describes the use of D-cycloserine, which was known to modulate the NMDA receptor, to improve and enhance memory and to treat cognitive deficits linked to a neurological disorder. D-cycloserine is described as a glycine agonist which binds to the strychnine-insensitive glycine receptor.

U.S. Pat. No. 5,061,721, issued to Cordi et al., and incorporated herein by reference, describes the use of a combination of D-cycloserine and D-alanine to treat Alzheimer's disease, age-associated memory impairment, learning deficits, and psychotic disorders, as well as to improve memory or learning in healthy individuals. D-alanine is administered in combination with D-cycloserine to reduce the side effects observed in clinical trials of D-cycloserine, mainly those due to its growth-inhibiting effect on bacteria resulting in depletion of natural intestinal flora. D-Alanine reverses the growth-inhibiting effect of D-cycloserine on bacteria. It is also reported that D-cycloserine actually has partial agonist character.

U.S. Pat. No. 5,086,072, issued to Trullas et al., and incorporated herein by reference, describes the use of 1-aminocyclopropanecarboxylic acid (ACPC), which was known to modulate the NMDA receptor as a partial agonist of the strychnine-insensitive glycine binding site, to treat mood disorders including major depression, bipolar disorder, dysthymia and seasonal effective disorder. It is also therein described that ACPC mimics the actions of clinically effective antidepressants in animal models. In addition, a co-pending U.S. patent application is cited that describes that ACPC and its derivatives may be used to treat neuropharmacological disorders resulting from excessive activation of the NMDA receptor. However, there remains a need in the art for a satisfactory method of modulating NMDA receptor function.

Development of drugs targeting the NMDA receptor, although desirous, has been hindered because the structure of the NMDA receptor has not yet been completely elucidated. It is believed to consist of several protein chains (subunits) embedded in the postsynaptic membrane. The first two subunits determined so far form a large extracellular region which probably contains most of the allosteric binding sites, several transmembrane regions looped and folded to form a pore or channel which is permeable to $Ca^{2+}$ and a carboxyl terminal region with an as yet unknown function. The opening and closing of the channel is regulated by the binding of various ligands to domains of the protein residing on the extracellular surface and separate from the channel. As such, these ligands are all known as allosteric ligands. The binding of two co-agonist ligands (glycine and glutamate) is thought to effect a conformational change in the overall structure of the protein which is ultimately reflected in the channel opening, partially open, partially closed, or closed. The binding of other allosteric ligands modulates the conformational change caused or effected by glutamate and glycine. It is believed that the channel is in constant motion, alternating between a cation passing (open) and a cation blocking (closed) state. It is not known at present whether the allosteric modulators actually increase the time during which the channel is open to the flow of ions, or whether the modulators increase the frequency of opening. Both effects might be occurring at the same time.

Several compounds are known which are antagonistic to the flow of cations through the NMDA receptor but which do not competitively inhibit the binding of allosteric ligands to any of the known sites. Instead, these compounds bind inside the open cation channel and are generally known as channel blockers. In fact, binding of a tritiated form of one such channel blocker, dizocilpine (i.e., MK-801), is a good measure of the activation of the NMDA receptor complex. When the channel is open, MK-801 may freely pass into the channel and bind to its recognition site in the channel. Conversely, when the channel is closed, MK-801 may not freely pass into the channel and bind. When the channel is partially closed, less MK-801 is able to bind than when the channel is fully open.

Channel blockers such as MK-801 and antagonists are known to protect cells from excitotoxic death but, in their case, the cure may be as undesirable as the death since they block any flux of $Ca^{2+}$ thereby eliminating any chance of resumed normal activity. Channel blockers and glutamate site antagonists are known to cause hallucinations, high blood pressure, loss of coordination, vacuolation in the brain, learning disability and memory loss. PCP, a typical channel blocker, produces a well characterized schizophrenic state in man.

Other divalent cations such as $Mg^{2+}$ and $Zn^{2+}$ can modulate the NMDA receptor. The exact location of the divalent cation binding site(s) is still unclear. $Zn^{2+}$ appears to be antagonistic to channel opening and appears to bind to an extracellular domain. $Mg^{2+}$ shows a biphasic activation curve—at low concentrations it is an agonist for NMDA receptor function, and at high concentrations it is a receptor antagonist. It appears to be absolutely necessary for proper receptor functioning and appears to bind at two sites—a voltage dependant binding site for $Mg^{2+}$ within the channel and another non-voltage dependent binding site on the extracellular domain. These compounds can modulate the NMDA receptor but are not appropriate for long-term therapy.

Furthermore, as recited, glutamate activates the NMDA receptor, increasing levels of intracellular calcium, which leads to activation of proteases, lipases, and other mediators of cell injury. The increasing levels of cellular calcium also results in membrane depolarization and spreading depression, further increasing energy demands and extracellular glutamate. Nitric oxide and other free radicals are generated that damage DNA, proteins, and fatty acids. A variety of neurological and inflammatory disorders may result from the increased levels of cellular calcium.

Thus, there is a need in the art for safe and effective compounds for modulating the $Ca^{2+}$ flow through the NMDA ion channel for preventing the overproduction of nitric oxide and other free radicals.

SUMMARY OF THE INVENTION

The present invention provides compounds that can be used in the treatment of neurological diseases that result from the overproduction of nitric oxide and other free radicals. The compounds are of the following formulas or pharmaceutically acceptable salts thereof:

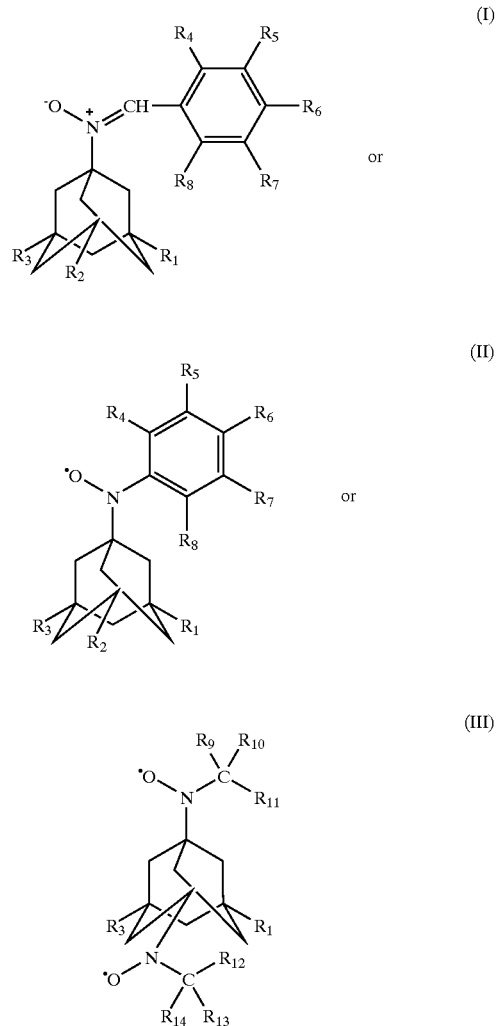

wherein:

$R_1$ and $R_3$ are H, OH, alkyl, cycloalkyl, amino or aryl, and can be the same or different;

$R_2$ is H, $NH_2$, alkyl, OH, COOH, amino, amide, or carbamate;

$R_4$–$R_8$ are H, OH, $NH_2$, alkyl, OH, COOH, ester, amino, amide, or alkyloxy, and can be the same or different; and $R_9$–$R_{14}$ are H, alkyl, or phenyl, and can be the same or different.

When any of $R_1$–$R_8$ is amino, the compounds are the free bases and their acid addition salts, such as HCl and $H_2SO_4$.

In preferred embodiments of the compounds of formulas (I) and (II), $R_1$, $R_3$–$R_{14}$ are independently H, methyl, ethyl or propyl, and $R_2$ is $NH_2$. In preferred compounds of formula (III), $R_1$, $R_3$–$R_{14}$ are independently H, methyl, ethyl or propyl.

The present invention also provides a method of treating and/or preventing neurological disorders that result from the overproduction of nitric oxide and other free radicals. The method comprises administering to a patient an effective amount of a pharmaceutically acceptable carrier and one of more of the compounds of the following formulas, or pharmaceutically acceptable salts thereof:

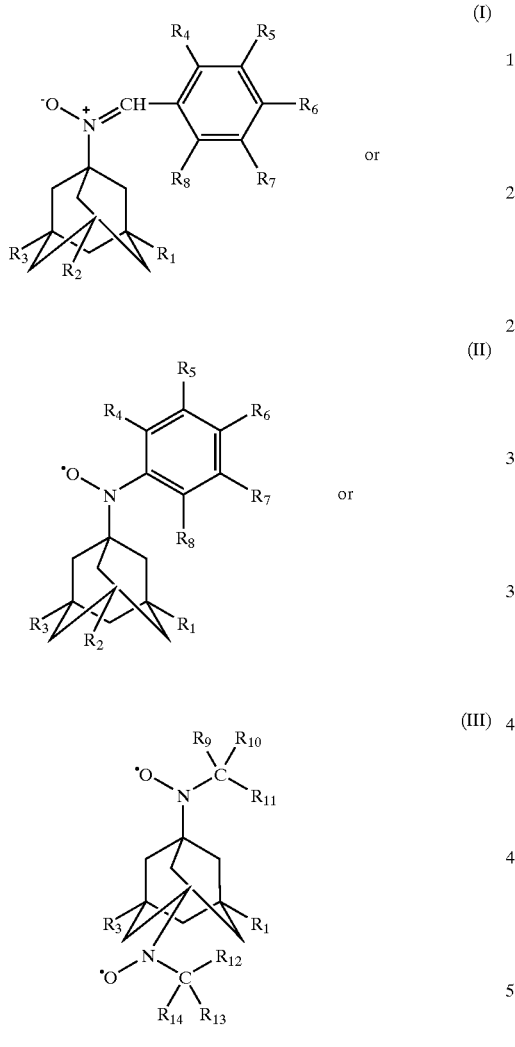

wherein:

$R_1$ and $R_3$ are H, OH, alkyl cycloalkyl, amino or aryl, and can be the same or different;

$R_2$ is H, $NH_2$, alkyl, OH, COOH, amino, amide, or carbamate;

$R_4$–$R_8$ are H, OH, $NH_2$, alkyl, OH, COOH, ester, amino, amide, or alkyloxy, and can be the same or different;

$R_9$–$R_{14}$ are H, alkyl, or phenyl, and can be the same or different.

When any of $R_1$–$R_8$ is amino, the compounds are the free bases and their acid addition salts, such as HCl and $H_2SO_4$.

The compounds of formulas (I), (II) and (III) are adamantane derivatives. The compound of formula (I) is a nitrone adamantane derivative and the compounds of formulas (II) and (III) are nitroxide adamantane derivatives. Like other adamantane derivatives, these compounds have been shown to be NMDA-receptor antagonists.

The present invention also provides a method of treating and/or preventing inflammatory diseases and disorders that result from the overproduction of nitric oxide and other free radicals. The method comprises administering to a patient an effective amount of a pharmaceutically acceptable carrier and one of more of the compounds of the following formulas, or pharmaceutically acceptable salts thereof:

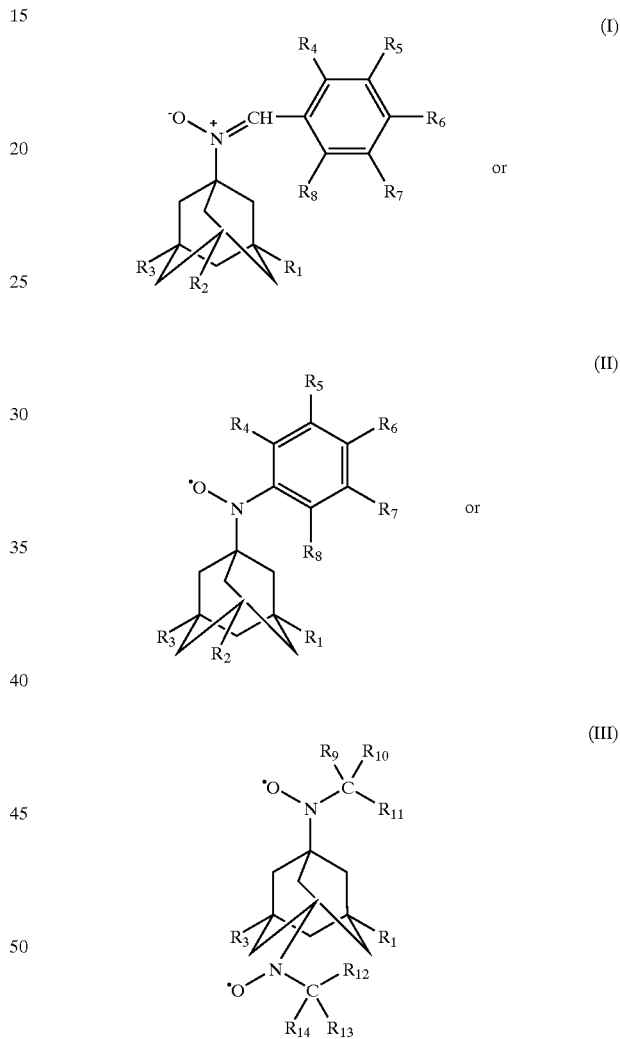

wherein:

$R_1$ and $R_3$ are H, OH, alkyl, cycloalkyl, amino or aryl, and can be the same or different;

$R_2$ is H, $NH_2$, alkyl, OH, COOH, amino, amide, or carbamate;

$R_4$–$R_8$ are H, OH, $NH_2$, alkyl, OH, COOH, ester, amino, amide, or alkyloxy, and can be the same or different;

$R_9$–$R_{14}$ are H, alkyl, or phenyl, and can be the same or different.

When any of $R_1$–$R_8$ is amino, the compounds are the free bases and their acid addition salts, such as HCl and $H_2SO_4$.

The present invention also provides a method of treating and/or preventing age-related disorders that result from the overproduction of nitric oxide and other free radicals. The method comprises administering to a patient an effective amount of a pharmaceutically acceptable carrier and one of more of the compounds of the following formulas, or pharmaceutically acceptable salts thereof:

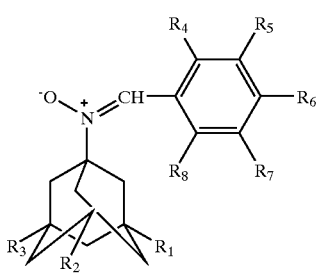

(I)

or

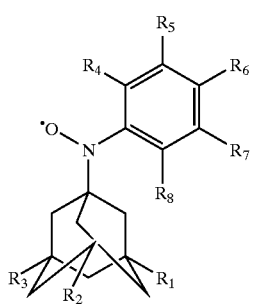

(II)

or

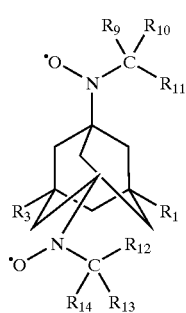

(III)

wherein:

$R_1$ and $R_3$ are H, OH, alkyl, cycloalkyl, amino or aryl, and can be the same or different;

$R_2$ is H, $NH_2$, alkyl, OH, COOH, amino, amide, or carbamate;

$R_4$–$R_8$ are H, OH, $NH_2$, alkyl, OH, COOH, ester, amino, amide, or alkyloxy, and can be the same or different;

$R_9$–$R_{14}$ are H, alkyl, or phenyl, and can be the same or different.

When any of $R_1$–$R_8$ is amino, the compounds are the free bases and their acid addition salts, such as HCl and $H_2SO_4$.

The present invention also provides for the use of NMDA receptor antagonist compounds that are formulated into medicaments used in the treatment of patients suffering from disorders that result from the overproduction of nitric oxide and other free radicals. The NMDA receptor antagonist compounds are of the following formulas or pharmaceutically acceptable salts thereof:

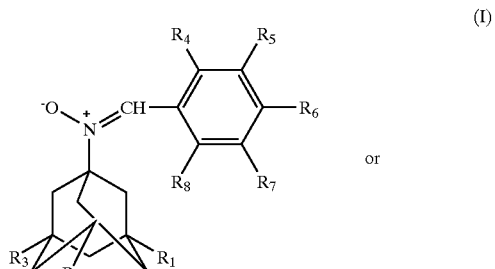

(I)

or

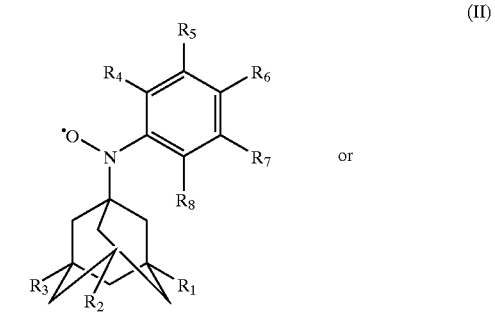

(II)

or

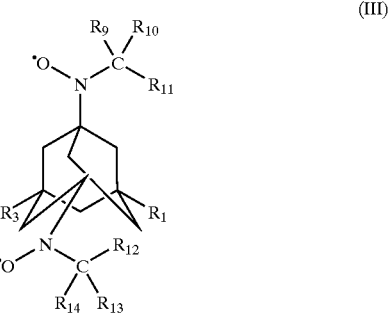

(III)

wherein:

$R_1$ and $R_3$ are H, OH, alkyl, cycloalkyl, amino or aryl, and can be the same or different;

$R_2$ is H, $NH_2$, alkyl, OH, COOH, amino, amide, or carbamate;

$R_4$–$R_8$ are H, OH, $NH_2$, alkyl, OH, COOH, ester, amino, amide, or alkyloxy, and can be the same or different;

$R_9$–$R_{14}$ are H, alkyl, or phenyl, and can be the same or different.

When any of $R_1$–$R_8$ is amino, the compounds are the free bases and their acid addition salts, such as HCl and $H_2SO_4$.

The present invention also provides pharmaceutical compositions that can be used to treat patients suffering from disorders that result from the overproduction of nitric oxide and other free radicals. The NMDA receptor antagonist compounds are of the following formulas or pharmaceutically acceptable salts thereof:

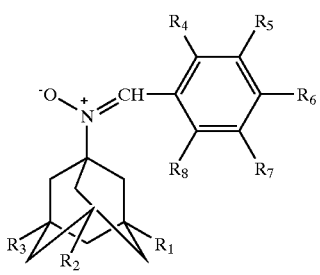

(I)

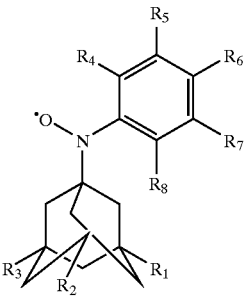

(II)

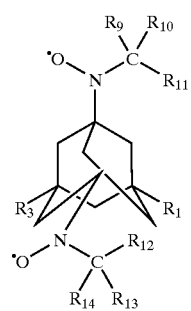

(III)

wherein:
R$_1$ and R$_3$ are H, OH, alkyl, cycloalkyl, amino or aryl, and can be the same or different;
R$_2$ is H, NH$_2$, alkyl, OH, COOH, amino, amide, or carbamate;
R$_4$–R$_8$ are H, OH, NH$_2$, alkyl, OH, COOH, ester, amino, amide, or alkyloxy, and can be the same or different;
R$_9$–R$_{14}$ are H, alkyl, or phenyl, and can be the same or different.

When any of R$_1$–R$_8$ is amino, the compounds are the free bases and their acid addition salts, such as HCl and H$_2$SO$_4$.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

FIG. 2 illustrates studies with memantine, indicative of its activating and/or antidepressant and neurological properties.

DETAILED DESCRIPTION OF THE INVENTION

Figure 1:
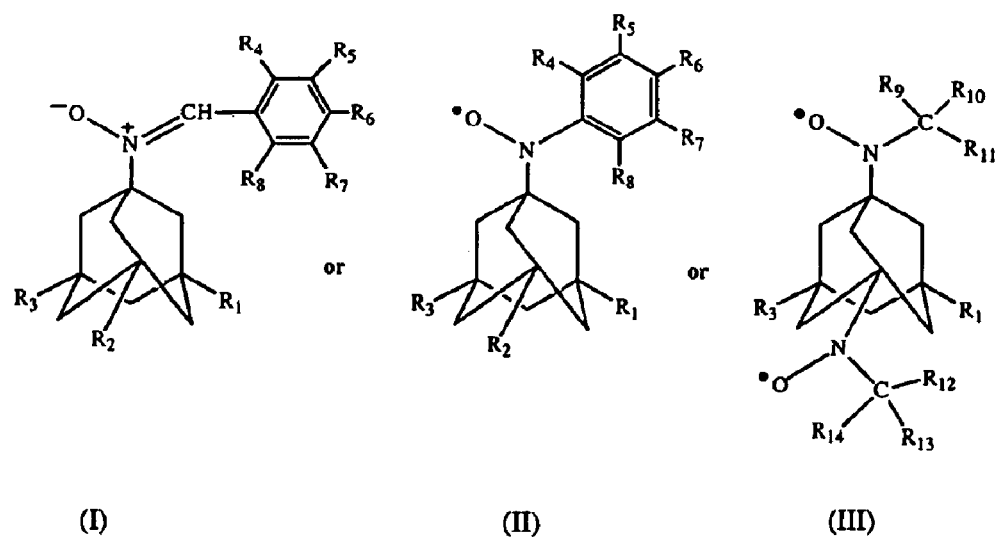
FIG. 1 shows the compounds of the present invention.

The present invention provides compounds of the formula:

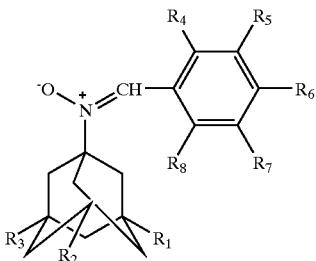

(I)

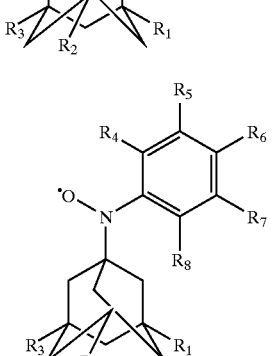

(II)

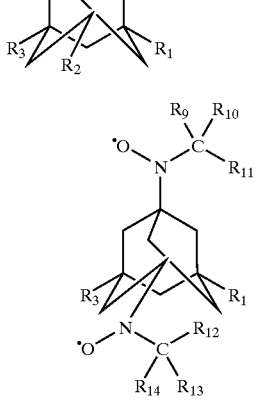

(III)

wherein:
R$_1$ and R$_3$ are H, OH, alkyl, cycloalkyl, amino or aryl, and can be the same or different;
R$_2$ is H, NH$_2$, alkyl, OH, COOH, amino, amide, or carbamate;
R$_4$–R$_8$ are H, OH, NH$_2$, alkyl, OH, COOH, ester, amino, amide, or alkyloxy, and can be the same or different;
R$_9$–R$_{14}$ are H, alkyl, or phenyl, and can be the same or different.

When any of R$_1$–R$_8$ is amino, the compounds are the free bases and their acid addition salts, such as HCl and H$_2$SO$_4$.

In preferred embodiments of the compounds of formulas (I) and (II), R$_1$, R$_3$–R$_{14}$ are independently H, methyl, ethyl or propyl, and R$_2$ is NH$_2$. In preferred compounds of formula (III), R$_1$, R$_3$–R$_{14}$ are independently H, methyl, ethyl or propyl.

The compounds of the present invention are effective for treating and/or preventing conditions associated with and disorders resulting from reactive oxygen species. The novel compounds of the present invention are NMDA receptor antagonists with antioxidant properties. As a result of their antioxidant properties these compounds are useful in the prevention and treatment of neurological disorders, inflammatory diseases and aging and age-related diseases.

As used herein, the term "Alkyl" refers to unsubstituted or substituted linear, branched or cyclic alkyl carbon chains of up to 15 carbon atoms. Linear alkyl groups include, for example, methyl, ethyl, N-propyl, N-butyl, N-pentyl, N-hexyl, N-heptyl and N-octyl. Branched alkyl groups include, for example, iso-propyl, sec-butyl, iso-butyl, tert-butyl and neopentyl. Cyclic alkyl ("cycloalkyl") groups include, for example, cyclopropyl, cyclobutyl, cyclopentyl and cyclohexyl. Alkyl groups can be substituted with one or more substituents. Nonlimiting examples of such substituents include $NO_2$, $ONO_2$, F, Cl, Br, I, OH, $OCR_3$, $CO_2H$, $CO_2CH_3$, CN, aryl and heteroaryl. Where "alkyl" is used in a context such as "alkyl—$ONO_2$," it refers to an alkyl group that is substituted with a $ONO_2$ moiety. Where "alkyl" is used in a context such as "C(O)alkyl-$ONO_2$," it refers to an alkyl group that is connected to a carbonyl group at one position and that is substituted with a $ONO_2$ moiety.

As used herein, the term "Heteroalkyl" refers to unsubstituted or substituted linear, branched or cyclic chains of up to carbon atoms that contain at least one heteroatom (e.g., nitrogen, oxygen or sulfur) in the chain. Linear heteroalkyl groups include, for example, $CH_2CH_2OCH_3$, $CH_2CH_2N(CH_3)_2$ and $CH_2CH_2SCH_3$. Branched groups include, for example, $CH_2CH(OCH_3)CH_3$, $CH_2CH(N(CH_3)_2)CH_3$ and $CH_2CH(OCH_3)CH_3$. Cyclic heteroalkyl groups include, for example, $CH(CH_2CH_2)_2O$, $H(CH_2CH_2)_2NCH_3$ and $CH(CH_2CH_2)_2S$. Heteroalkyl groups can be substituted with one or more substituents. Nonlimiting examples of such substituents include $NO_2$, $ONO_2$, F, Cl, Br, I, OH, $OCR_3$, $CO_2H$, $CO_2CH_3$, CN, aryl and heteroaryl. Where "heteroalkyl" is used in a context such as "heteroalkyl-$ONO_2$," it refers to a heteroalkyl group that is substituted with an $ONO_2$ moiety. Where "heteroalkyl" is used in a context such as "C(O)heteroalkyl-$NO_2$," it refers to an alkyl group that is connected to a carbonyl group at one position and that is substituted with a $ONO_2$ moiety.

As used herein, the term "Aryl" refers to an unsubstituted or substituted aromatic, carbocyclic group. Aryl groups are either single ring or multiple condensed ring compounds. A phenyl group, for example, is a single ring, aryl group. An aryl group with multiple condensed rings is exemplified by a naphthyl group. Aryl groups can be substituted with one or more substituents. Nonlimiting examples of such substituents include $NO_2$, $ONO_2$, F, Cl, Br, I, OH, $OCR_3$, $CO_2H$, $CO_2CH_3$, CN, aryl and heteroaryl.

As used herein, a "therapeutic effect" refers to an observable improvement over the baseline clinically observable signs and symptoms of a neurological, inflammatory, aging-related or neuropsychiatric disorder, as measured by the techniques disclosed herein.

The term "pharmaceutically acceptable" refers to a lack of unacceptable toxicity in a compound, such as a salt or excipient. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, citrate, and the like. Pharmaceutically acceptable excipients are described at length by E. W. Martin, in *Remington's Pharmaceutical Sciences* Mack Publishing Company (1995), Philadelphia, Pa., 19th ed.

As used herein, a "neuropsychiatric disorder" refers to acute and subacute disorders with both neurological and psychiatric features. Examples of common neuropsychiatric disorders that are treatable by the present invention comprise major depressive disorder (MDD), bipolar disorder (manic-depressive illness or BPD), anxiety, and drug addiction including dependence, withdrawal, and drug tolerance, disorders arising from trauma, ischemic or hypoxic conditions including stroke, hypoglycemia, cerebral ischemia, cardiac arrest, spinal cord trauma, head trauma, perinatal hypoxia, cardiac arrest and hypoglycemic neuronal damage, epilepsy, Alzheimer's disease, Huntington's disease, Parkinsonism, amyotrophic lateral sclerosis, convulsion, pain, schizophrenia, muscle spasms, migraine headaches, urinary incontinence, emesis, brain edema, tardive dyskinesia, AIDS-induced dementia, ocular damage, retinopathy, cognitive disorders, and neuronal injury associated with HIV-infection such as dysfunction in cognition, movement and sensation. Neuropsychiatric disorders are described in Diagnostic and Statistical Manual of Mental Disorders, 4th Ed., American Psychiatric Press, (1994) incorporated herein by reference.

Certain adamantane derivatives, such as memantine, have been shown success in eliminating free radicals and reducing oxidative stress caused by free radicals. Memantine (Akatinol Memantine®, (Merz & Co., GmbH) CAS Registry No. 41100-52-1), which has the structure:

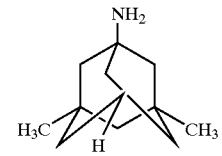

is an uncompetitive N-methyl-D-aspartate (NMDA) antagonist currently used for the treatment of dementia syndrome, spinal spasticity and Parkinson's disease.

Chemically, memantine is 1-amino-3,5-dimethyladamantane of the adamantane class. Compared to the other NMDA antagonists, memantine has been reported to have the greatest effective potency for binding at the PCP and MK-801 receptor sites in human brain tissue (Kornhuber et al., *Eur J Pharmacol* (*Mod Pharmacol Sect*) 1991;206: 297–300). Memantine binds to the PCP and MK-801 binding sites of the NMDA receptor in postmortem human frontal cortex at therapeutic concentrations (Kornhuber et al., *Eur J Pharmacol* 1989;166: 589–590), and reduces membrane currents (Bormann, *Eur J Pharmacol* 1989;66: 591–592). Memantine is well tolerated, and despite its wide use in Germany, only a few isolated cases of psychosis and cognitive deficits have been reported with its use. Compared to other NMDA antagonists, memantine appears to have a more favorable pharmacological profile and is less likely to induce psychosis and cognitive deficits. Without being bound by theory, one possibility why memantine is less likely to induce cognitive deficits and psychosis may be due its negligible effects on the hypothalamic-pituitary axis (HPA) compared to other NMDA antagonists such as ketamine. NMDA receptors have been reported to be involved in the physiologic pulsatile regulation of hormone release from the HPA axis (Bhat et al., 1995) resulting in hypercortisolemia. Psychotic symptoms and cognitive deficits in depression has been linked to an increased dopamine activity secondary to this HPA overactivity (Walder et al., *Biol Psychiatry* 2000;48: 1121–1132). The lack of memantine's effect on the HPA axis and resulting increased dopamine activity may be an explanation for the low rates of psychosis seen with this drug. Another advantage of memantine over other NMDA antagonists is that contrary to, for example, dextromethorphan, memantine has no active metabolites that possess NMDA antagonizing properties (Ziemann et al., 1996). Furthermore, memantine serum levels are available for measurement. Memantine is one of the few NMDA antagonists available for use in humans and is ideal for treating major depression as it and its precursors amantadine, have been in clinical use for many years with minimal side-effects (Kornhuber et al., *J Neural Transm Suppl* 1994;43: 91–104). Rarely has memantine been associated with significant the side-effects of agitation, confusion, and psychosis (Rabey et al., *J Neural Transm* 1992;4: 277–282; Riederer et al., *Lancet*, 1991 Oct. 19; 338(8773):1022–3) as seen with other NMDA antagonists, such as phencyclidine and ketamine. Memantine is well tolerated in the geriatric populations for which it is typically prescribed in Europe (Görtelmeyer et al., *Arzneim-Forsch/Drug Res* 1992;42: 904–913).

Memantine has significant neurotrophic and activating properties, and it can be used to modulate glutamatergic neurotransmission, while also providing for robust neurotrophic effects via direct intracellular mechanisms. Memantine displays potent non-competitive voltage-dependent NMDA antagonist properties with effects comparable to MK-801 (see, Bormann, *Eur J Pharmacol* 1989;66: 591–592, incorporated herein by reference). Memantine also demonstrates anticonvulsant and neuroprotective properties and dopaminergic effects in vitro (see, Maj, *Arzneim Forsch/Drug Res* 1982;32: 1236–1273, incorporated herein by reference). Memantine has been used since 1978 and is approved in Germany for the treatment of mild and moderate cerebral performance disorders with the following cardinal symptoms: concentration and memory disorders, loss of interest and drive, premature fatigue, and dementia syndrome, as well as in diseases in which an increase of attention and alertness (vigilance) is required. Cerebral and spinal spasticity, Parkinson and Parkinson-like diseases are other indications. Memantine acts as a modulator of glutamatergic neurotransmission. In the states of a reduced glutamate release, after degeneration of neurons, memantine results in an improvement in signal transmission and activation of neurons. In the state of a massive glutamate release, e.g., ischemia, memantine blocks NMDA receptors that mediate the excitotoxic action of glutamate on neurons. It is believed that its neuroprotective properties are due to NMDA receptor antagonism in pathologies with increased glutamate. Memantine's efficacy in Parkinson's disease has been suggested to be a result of its ability to neutralize (or modulate) the increased activity of the glutamatergic cortico-striatal and subthalamicopallidal pathways (Klockgether and Turski, *Trends Neurosci* 1989;12: 285–286; *Ann Neurol* 1990;28: 539–546, and Schmidt et al., *Trends Neurosci* 1990;13: 46–47., incorporated herein by reference). This effect is independent of dopamine or norepinephrine release.

Memantine has been reported for many years to have positive effects on deficit symptoms or depressive symptoms commonly found in other neuropsychiatric disorders such as Parkinson's disease and dementia. In studies of patients with dementia and Parkinson's disease, the symptoms of depressed mood, anxiety, lack of drive, somatic disturbances, impairment in vigilance, short-term memory and concentration were significantly improved with memantine. Some of these studies also reported the adverse events of hyperactivity, restlessness, and euphoria with memantine, suggesting that it may have activating or antidepressant properties. These findings are summarized in the table shown in FIG. 2.

Other adamantane derivatives have been proven effective to treat a variety of afflictions, such as Rimantadine (1-(1-aminoethyl)adamantane), for the prophylaxis and treatment of influenza in humans, and Amantadine (1-amino adamantane) has been used for the treatment of both influenza and Parkinson's disease (Schwab et al., *J. Am. Med. Assoc.* (1969) 208:1168).

Nitric oxide ("NO") plays important roles in the homeostatic regulation of blood pressure, blood clotting and neurotransmission. NO also serves as part of the host defense system against cancer cells, parasites and microbes. In the brain, NO is produced in cerebellar granule cells in respond to stimulation of the NMDA subtype of glutamate receptors. (Garthwaite et al., *Nature*, 336: 385, 1988). In neuronal cells, an isoform of the enzyme nitric oxide synthase (NOS) is activated by the influx of $Ca^{2+}$ via NMDA receptor-operated ion channels. (Bredt, et al., *Nature*, 347:768, 1990). NO diffuses out and acts upon one or more neighboring structures, including the presynaptic nerve cell and thus strengthens the connection between the cells on the two sides of the synapse. Thus NOS is part of a feedback loop or a retrograde messenger. NO down-regulates NOS via this mechanism. The influx of $Ca^{2+}$ through the NMDA ion channel is also inhibited by this feedback mechanism.

NO is produced in vascular endothelium and diffuses from endothelial cells to the adjacent smooth muscle cells activating soluble guanylate cyclease (sGC) which catalyzes the synthesis of cyclic guanosine monophosphate (c-GMP). The latter mediates further signal transduction and leads to vasorelaxation. NO also inhibits platelet aggregation via the sGC-cGMP-dependent pathway. Together with prostacyclin, NO provides a defense against platelet aggregation and adhesion to the endothelium. Thus, proper function of the endothelium and NO is important for prevention of atherosclerosis and heart disease amongst other inflictions.

Nitrone and nitroxides are cell permeable and stable free radicals. Nitrone reacts with free radicals to form nitroxide which acts as superoxide dismutase and which mimics and catalyzes the dismutation of superoxide anion (Samuni et al., *J. Biol. Chem.* 263: 17921, 1988; Krishna et al., *J. Biol. Chem.* 271: 26018, 1996; Krishna et al., *J. Biol. Chem.* 271: 26026, 1996) and stimulates the catalase-like activity of hemeproteins (Krishna et al., *J. Biol. Chem.* 271: 26026, 1996) resulting in protection of cells from free radical mediated damage. One additional advantage of nitroxide over other antioxidants is that its concentration remains the same before and after the reaction because it acts as a catalyst. For example, phenyl-tert-butyl nitrone (PBN) reacts with free radicals to form nitroxide:

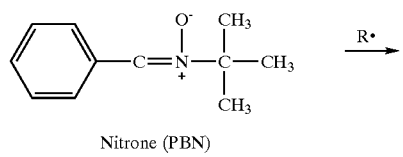

Nitrone (PBN)

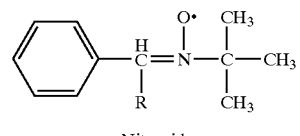

Nitroxide

Nitroxide removes free radicals by reacting with free radicals directly or by oxidizing the reduced metals thereby inhibiting the Fenton and the metal-catalyzed Haber-Weiss reactions (Mohsen et al., *Mol. Cellul. Biochem.* 145:103, 1995). For example, 2,2,6,6-tetramethylpiperidine-1-oxyl (TEMPOL) removes superoxide ($O_2^{\cdot-}$) in the following manner:

1.

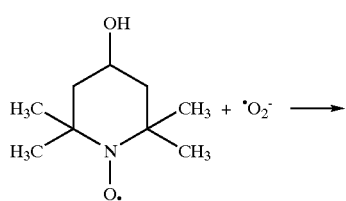

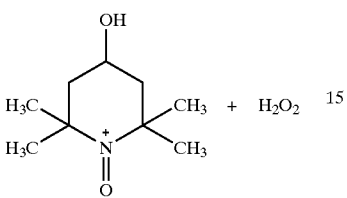

2.

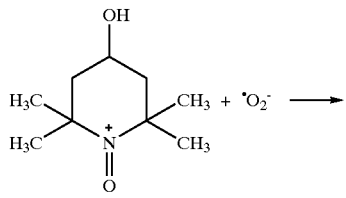

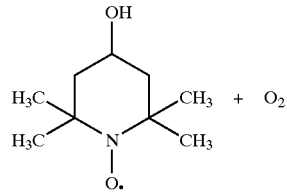

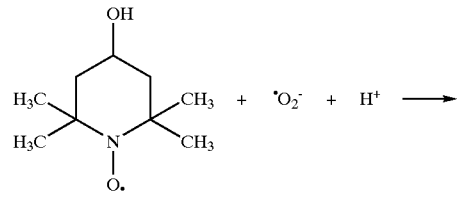

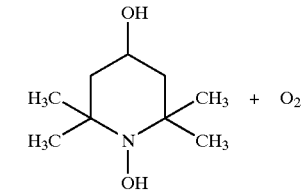

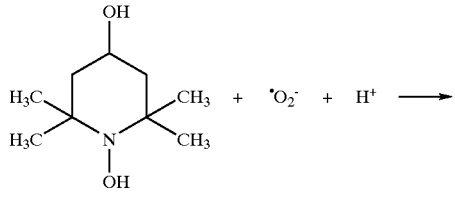

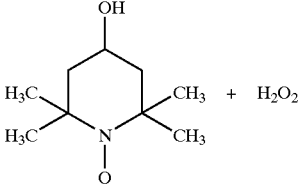

3.

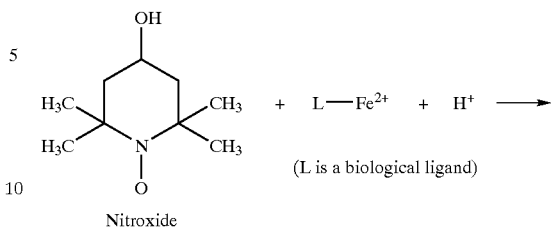

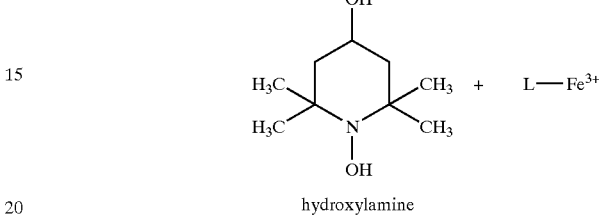

The terminal products of the reaction of nitrone with free radicals include hydroxylamine derivatives, aldehydes and amines. These products are much less damaging to cells than free radicals (Chamulitrat et al., *J. Biol. Chem.* 268: 11520, 1993; Janzen et al., *Free Rad. Biol. Med.* 12:169, 1992; Kotake and Janzen, *J. Am. Chem. Soc.* 113:948, 1991). Daily intraperitoneal injection of PBN to sensescence accelerated mouse resulted in a 33% increase of life span (Edamatsu et al., *Biochem. Biophys. Res. Commun.* 211:847, 1995). When 24-month old rats were intraperitoneally injected with PBN at a dose of 32 mg/kg daily for 9.5 months, lipid peroxidation within two brain areas important for cognitive function, the neocortex and the globus pallidus, were reduced and the cognitive performance of the aged rats were improved. More impressively, at 32 months into the study, 7 of 11 PBN-treated rats were still alive (Sack et al., *Neurosci. Lett.* 205:181, 1996).

In another experiment, the nitroxide, 4-hydroxy-2,2,6,6-tetramethylpiperidine-1-oxyl alleviated heat hyperalgesia in rats with an experimental painful peripheral neuropathy (Tal, *Neuroreport* 7:13183, 1996). In isolated rat heart, nitroxide strongly protected against reperfusion injury by preventing the formation of hydroxyl radical (•OH) and not by decreasing heart rate or by direct suppression of arrhythmia (Gelvan et al., *Proc. Natl. Acad. Sci.* 88:4680 1991). Nitroxide afforded full protection of cardiomycytes of rats in culture in millimolar concentration without toxic side-effects from the toxicity of hydrogen peroxide (Mohsen et al., *Mol. Cellul. Biochem.* 145:103, 1995). This data demonstrated the usefulness of free radical-trapping nitrone and nitroxide as therapeutic agents for human diseases or preventive agents for aging.

Agonists of glutamate receptors of the N-methyl-D-aspartate (NMDA) type potentially have a wide range of use in the treatment of various neurological diseases. Memantine was found to be a micromolar antagonist of the NMDA receptor (Borman, *Eur. J. Pharmacol.* 166:591, 1989). Memantine protects cortical and retinal neuron cultures from the toxicity of glutamate, NMDA and the HIV-1 coat protein gp120 (Deyer et al., *Science* 248:364, 1990). Memantine has antihypoxic properties in vitro and in vivo. Recent studies demonstrate that memantine also prevents quinolic acid-induced hippocampal damage in rats (Keilhoff et al., *Eur. J. Pharmacol.* 219:451, 1992). Although structurally quite different from other NMDA channel blockers, memantine inhibits [$^3$H]dizocilpine (Chen et al., *J. Neurosci.* 12: 4427, 1992) binding to brain membranes. Memantine also blocks other neurotransmitter-gated ionotropic receptors, including nicotinic acetylcholine receptors (Masou et al., *Eur. J. Pharmacol.* 130: 187, 1986) and 5-hydroxytryptamine 5-HT$_3$ receptors (Reiser et al., *Brain Res.* 443: 338, 1988).

Like memantine, MK-801 and ketamine also bind to NMDA receptors and have been shown to afford neuroprotection. Combination therapy with MK-801 and PBN protected ischemic neuronal damage in hippocampal slice much better than with either agent alone (Barth et al., *Exp. Neurol.* 141: 330, 1996). Therefore, the combination of NMDA antagonist function with free radical scavenger activity in one agent affords synergistic protection not provided by either agent alone.

The novel compounds of the instant invention include a nitrone adamantane derivative (formula (I)) and nitroxide adamantane derivatives (formulas (II) and (III)). The adamantane derivatives of formulas (I), (II) and (III) are NMDA receptor antagonists with antioxidant properties, which bind to NMDA receptors and regulate the NMDA receptor-operated ion channels limiting influx of $Ca^{2+}$, thereby preventing the overproduction of NO and other free radicals. Furthermore, they scavenge free radicals in neuronal cells including superoxide ($O_2^{\cdot-}$), peroxynitrite ($ONOO^-$) and hydroxyl radical (•OH). As a result, they may be useful in the prevention and treatment of neurological disorders including hypoxic-ischemic brain injury, trauma, epilepsy, Parkinson's disease, Huntington's disease, amyotrophic lateral sclerosis, and AIDS dementia, as well as other inflammatory diseases such as inflammatory bowel disease, rheumatoid arthritis, asthma, atherosclerosis, coronary heart disease, reperfusion injury from heart attack or stroke and other age-related diseases. They may also be useful in the prevention of aging.

The nitrone and nitroxide adamantane compounds of the present invention, and derivatives thereof, can be administered to a patient in the form of a pharmaceutically acceptable salt or in a pharmaceutical composition. A compound that is administered in a pharmaceutical composition is mixed with a suitable carrier or excipient such that a therapeutically effective amount is present. The term "therapeutically effective amount" refers to an amount of the compounds of the nitroxide or nitrone adamantane derivative that is necessary to achieve a desired endpoint (e.g., preventing the overproduction of nitric oxide and other free radicals, decreasing neuronal damage as the result of a stroke, etc.).

A variety of preparations can be used to formulate pharmaceutical compositions containing the nitroxide or nitrone adamantane derivatives, including solid, semi solid, liquid and gaseous forms. *Remington's Pharmaceutical Sciences*, Mack Publishing Company (1995), Philadelphia, Pa., 19$^{th}$ ed. Tablets, pills, granules, dragees, gels, slurries, ointments, solutions, suppositories, injections, inhalants and aerosols are examples of such formulations. The formulations can be administered in either a local or systemic manner or in a depot or sustained release fashion. Administration of the composition can be performed in a variety of ways. Among others, oral, buccal, rectal, parenteral, intraperitoneal, intradermal, transdermal and intratracheal means can be used.

Where the nitroxide or nitrone adamantane derivative is given by injection, it can be formulated by dissolving, suspending or emulsifying it in an aqueous or nonaqueous solvent. Vegetable or similar oils, synthetic aliphatic acid glycerides, esters of higher aliphatic acids and proylene glycol are examples of nonaqueous solvents. The compound is preferably formulated in aqueous solutions such as Hank's solution, Ringer's solution or physiological saline buffer.

Where the nitroxide or nitrone adamantane derivatives is given orally, it can be formulated through combination with pharmaceutically acceptable carriers that are well known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxyproylmethyl-cellulose, sodium carboxymethylcellulose and polyvinylpyrrolidone (PVP).

The nitroxide or nitrone adamantane derivatives of the present invention can also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Pharmaceutical compositions of the present invention contain a therapeutically effective amount of the nitroxide or nitrone adamantane derivative. The amount of the compound will depend on the patient being treated. The patient's weight, severity of illness, manner of administration and judgment of the prescribing physician should be taken into account in deciding the proper amount. The determination of a therapeutically effective amount of an aminoadamantane derivative is well within the capabilities of one with skill in the art.

Although a therapeutically effective amount of a nitroxide or nitrone adamantane derivative will vary according to the patient being treated, suitable doses will typically be in the range between about 0.1 mg and 1 g of the compound.

In some cases, it may be necessary to use dosages outside of the stated ranges to treat a patient. Those cases will be apparent to the prescribing physician. Where it is necessary, a physician will also know how and when to interrupt, adjust or terminate treatment in conjunction with a response of a particular patient.

Compounds of the invention may be tested for efficacy in reducing neuronal damage using the assay described below; an effective compound will cause a decrease in neuronal cell death. Compounds most preferred in the invention are those which effect the greatest protection of neurons from NMDA receptor-mediated injury, e.g., that injury resulting from stimulation of the NMDA receptor by glutamate (as shown below) or other excitatory amino acids or structurally similar compounds or from stimulation by excitatory peptides, such as N-acetyl aspartyl glutamate.

Assay for Neuronal Cell Function and Death

To test the nitroxide and nitrone adamantane derivatives for their ability to prevent neurotoxicity, neuronal cell death may be assayed as follows. Under general anesthesia, the fluorescent dye granular blue (Mackromolecular Chemin, Umstadt, FRG) is injected as approximately a 2% (w/v) suspension in saline into the superior colliculus of 4- to 6-day-old Long-Evans rats (Charles River Laboratory, Wilmington, Mass.). Two to 6 days later, the animals are sacrificed by decapitation and enucleated, and the retinas quickly removed. The retinas are dissociated by mild treatment with the enzyme papain and cultured in Eagle's minimum essential medium (MEM, catalog #1090, Gibco, Grand Island, N.Y.) supplemented with 0.7% (w/v) methylcellulose, 0.3% (w/v) glucose, 2 mM glutamine, 1 μg/ml gentamicin, and 5% (v/v) rat serum, as described in Lipton et al., J. Physiol. 385:361, 1987. The cells are plated onto 75 mm.sup.2 glass coverslips coated with poly-L-lysine in 35 mm tissue culture dishes. The candidate nitroxide or nitrone adamantane derivative is added (e.g., in a series of concentrations ranging from 1 nM–1 mM) in the presence or absence of compounds which activate the NMDA receptor-operated channel complex, and in high calcium, low magnesium medium (10 mM $CaCl_2$, 50 μM $MgCl_2$) to enhance NMDA-receptor neurotoxicity in this preparation (Hahn et al., Proc. Natl. Acad. Sci. USA 85:6556, 1988; Levy et al., Neurology 40:852, 1990; Levy et al., Neurosci. Lett. 110:291, 1990). The degree of survival (under these ionic conditions or with added exogenous NMDA (200.mu.M))is compared to that in normal medium (1.8 mM $CaCl_2$, 0.8 mM $MgCl_2$), which minimizes NMDA receptor-mediated injury in this preparation (Hahn et al., cited above). Incubations last 16–24 h at 37.degree. C. in an atmosphere of 5% $CO_2$/95% air. The ability of retinal ganglion cells to take up and cleave fluorescein diacetate to fluorescein is used as an index of their viability as described in detail in Hahn et al., (Proc. Natl. Acad. Sci. USA 85:6556, 1988). Dye uptake and cleavage generally correlate well with normal electrophysiological properties assayed with patch electrodes.

To perform the viability test, the cell-culture medium is exchanged for physiological saline containing 0.0005% fluorescein diacetate for 15–45 s, and then cells are rinsed in saline. Retinal ganglion cell neurons that do not contain the fluorescein dye (and thus are not living) often remain visible under both phase-contrast and UV fluorescence optics, the latter because of the continued presence of the marker dye granular blue; other dead retinal ganglion cells disintegrate, leaving only cell debris. In contrast, the viable retinal ganglion cells display not only a blue color in the UV light but also a yellow-green fluorescence with filters appropriate for fluorescein. Thus, the use of two exchangeable fluorescence filter sets permits the rapid determination of viable ganglion cells in the cultures. The ganglion cells are often found as solitary neurons as well as neurons lying among other cells in small clusters.

A nitroxide or nitrone adamantane derivative may be tested for utility in the method of the invention using any type of neuronal cell from the central nervous system, as long as the cell can be isolated intact by conventional techniques. In addition to the retinal cultures described above, we have also used hippocampal and cortical neurons, but any neuron can be used that possess NMDA receptors (e.g., neurons from other regions of the brain). Such neurons may be prenatal or postnatal, and they may be from a human, rodent or other mammals. In one example, retinal cultures can be produced from postnatal mammals; they are well-characterized and contain a central neuron, the retinal ganglion cell, that can be unequivocally identified with fluorescent labels. A substantial portion of retinal ganglion cells in culture display both functional synaptic activity and bear many, if not all, of the neurotransmitter receptors found in the intact central nervous system.

Measurement of Intracellular $Ca^{2+}$

The concentration of intracellular free $Ca^{2+}$ ($[Ca^{2+}]i$) is measured in neonatal cortical neurons by digital imaging microscopy with the $Ca^{2+}$ sensitive fluorescent dye fura 2, as follows. The same cortical neuronal cultures as described above are used. During $Ca^{2+}$ measurements, unless otherwise stated the fluid bathing the neurons consists of Hanks' balanced salts: 137.6 mM NaCl, 1 mM $NaHCO_3$, 0.34 mM $Na_2HPO_4$, 0.44 mM $KH_2PO_4$, 5.36 mM KCl, 1.25 mM $CaCl.sub.2$, 0.5 mM $MgSO_4$, 0.5 mM $MgCl_2$, 5 mM Hepes NaOH, 22.2 mM glucose, and sometimes with phenol red indicator (0.001% v/v); pH 7.2. NMDA (in the absence $Mg^{++}$), glutamate, and other substances are usually applied to the neurons by pressure ejection after dilution in this bath solution. Neuronal $[Ca^{2+}]i$ is analyzed with fura 2-acetoxymethyl ester (AM) as described [Grynkiewicz, et al., J. Biol. Chem. 260:3440 (1985); Williams et al., Nature 318:558 (1985); Connor et al., J. Neurosci. 7:1384 (1987); Connor et al., Science 240:649 (1988); Cohan et al., J. Neurosci. 7:3588 (1987); Mattson, et al., ibid, 9:3728 (1989)]. After adding Eagle's minimum essential medium containing 10 μM fura 2-AM to the neurons, the cultures are incubated at 37.degree. C. in a 5% $CO_2$/95% air humidified chamber and then rinsed. The dye is loaded, trapped, and deesterified within 1 hour, as determined by stable fluorescence ratios and the effect of the $Ca^{2+}$ ionophore ionomycin on $[Ca^{2+}]i$ is measured. During $Ca^{2+}$ imaging, the cells are incubated in a solution of Hepes-buffered saline with Hanks' balanced salts. The $[Ca^{2+}]i$ is calculated from ratio images that are obtained by measuring the fluorescence at 500 nm that is excited by 350 and 380 nm light with a DAGE MTI 66 SIT or QUANTEX QX-100 Intensified CCD camera mounted on a Zeiss Axiovert 35 microscope. Exposure time for each picture is 500 ms. Analysis is performed with a Quantex (Sunnyvale, Calif.) QX7-210 image-processing system. Since cells are exposed to ultraviolet light only during data collection (generally less than a total of 20 s per cell), bleaching of fura 2 is minimal. Delayed NMDA-receptor mediated neurotoxicity has been shown to be associated with an early increase in intracellular $Ca^{2+}$ concentration.

Correlation Between Channel-Blocking and Anticonvulsive Action

The correlation between the action of the tested nitroxide or nitrone adamantane derivatives at the NMDA receptor channel (in vitro) and the anticonvulsive effect (in vivo) has been tested. For this purpose an xy diagram of both test parameters is plotted. It shows that there is a correlation between the blocking of the NMDA receptor channel and the anticonvulsive action of the nitroxide or nitrone adamantanes of formula (I), (II) or (III).

Protection Against Cerebral Ischemia

Both carotid arteries are occluded in rats for 10 minutes. At the same time the blood pressure is reduced to 60–80 mg Hg by withdrawal of blood (Smith et al., 1984, Acta Neurol. Scand. 69: 385, 401). The ischemia is terminated by opening the carotids and reinfusion of the withdrawn blood. After seven days the brains of the test animals are histologically examined for cellular changes in the CA1–CA4 region of the hippocampus, and the percentage of destroyed neurons is determined. The action of the candidate nitroxide or nitrone adamantane derivative is determined after a single administration of 5 mg/kg and 20 mg/kg one (1) hour prior to the ischemia.

Figure 3:
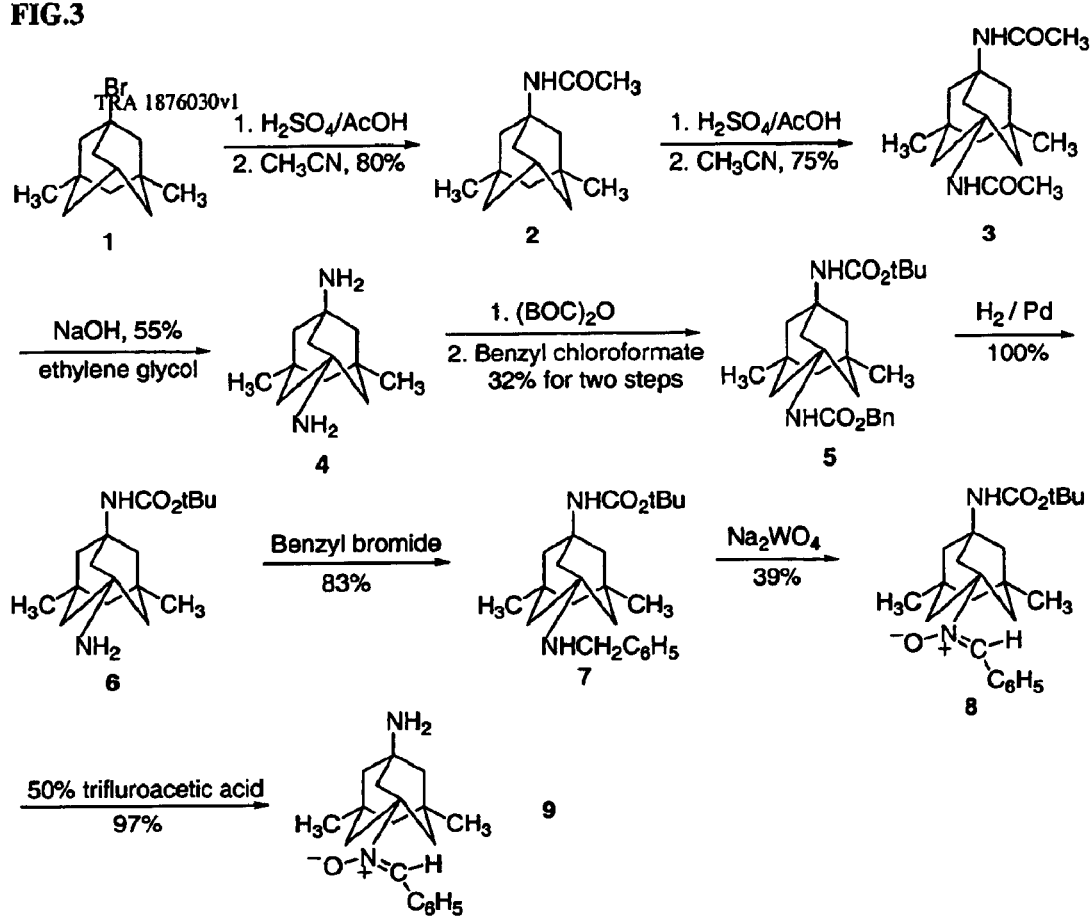
FIG. 3 shows an exemplary synthesis of one embodiment of a nitrone adamantane derivative in accordance with the present invention.

The following examples pertain to an exemplary synthesis of one embodiment of nitrone adamantane derivatives in accordance with the present invention as illustrated in FIG. 3.

EXAMPLE 1

Synthesis of 1,7-diacetamido-3,5-dimethyladamantane (3)

1-Acetamido-3,5-dimethyladamantane (2) (10 g) was added slowly to concentrated sulfuric acid (120 mL) cooled to 0° C. in a salt-ice bath. The solution was stirred at 0° C. for 1 h. Acetonitrile (23 mL) was then added dropwise. The reaction mixture was stirred at 0° C. for 2 h, and then at room temperature for 1 h. The reaction mixture was poured into ice-water. Saturated sodium hydroxide solution was added with cooling. The precipitate (dark solid) was filtered, and discarded. The off-white solid was collected by filtration. Recrystallization afforded 3 as a white solid (6.3 g).

EXAMPLE 2

Synthesis of 1,7-diamino-3,5-dimethyladamantane (4)

Diamide 3 (1.56 g) was added to diethyene glycol (25 mL). The reaction mixture was stirred at 175~180° C. for 16 h. The brown solution was cooled to room temperature, and water was added (100 mL). The reaction mixture was extracted with a solvent consisting of ethyl acetate (80%) and t-butylmethyl ether (20%) (70 mL×7). The combined organic solvent was washed with water and brine, and dried over sodium sulfate. The solution was concentrated to approximately 20 mL. Anhydrous hydrogen chloride in ethyl acetate was added. The precipitate was filtered. The product was then dissolved in water (10 mL). The product was extracted with ethyl acetate (10 mL×6). Solvent was removed to afford diamine 4 as an off-white solid (767 mg).

EXAMPLE 3

Synthesis of 1-tert-butoxycarbonylamino-7-benzyloxycarbonylamino-3,5-dimethyladamantane (6)

Di-tert-butyl-dicarbonate (23 mg) was added to diamine 4 (23 mg) dissolved in tetrahydrofuran (THF) cooled to 0° C. The reaction mixture was stirred at room temperature overnight. Benzyl chloroformate (25 mg) was added, and the reaction mixture was stirred at room temperature for 2 h. THF was removed. The residue was dissolved in ethyl acetate, and washed with water. The solution was dried over sodium sulfate, and solvent was removed. The product was purified by thin layer chromatography, eluting with a mixture of ethyl acetate and hexane (1/3, v/v) to afford 6 as a white solid (20 mg).

EXAMPLE 4

Synthesis of 1-tert-butoxycarbonylamino-7-benzylamino-3,5-dimethyladamantane (7)

Diamide 6 (43 mg) was dissolved in THF (2 mL) and MeOH (2 mL). To this solution was added Pd/C (10 mg). The protecting group was removed by hydrogenation over hydrogen for 1 h. The reaction mixture was filtered. Solvent was removed to give a white solid (monoamine). Without further purification, dimethylformamide (1 mL) was added, followed by benzyl bromide and sodium hydrogen carbonate. The reaction mixture was stirred at room temperature overnight. The product was extracted with ethyl acetate, and purified by thin layer chromatography, eluting with a mixture of ethyl acetate and hexane (1/1, v/v) to afford 7 as a light yellow oil (18 mg).

EXAMPLE 5

Synthesis of α-phenyl-N-(7-tert-butoxycarbonylamino-3,5-dimethyladamantane) nitrone (8)

To 7 (54 mg) in methanol was added $Na_2WO_4$ (18 mg) and 30% $H_2O_2$ (80 mg), respectively, at room temperature.

The solution was stirred for 2 h. Solvent was removed in vacuo to give a residue. The latter was treated with a saturated $Na_2S_2O_4$ solution (4 mL). The product was extracted with tert-butyl methyl ether, and purified by thin layer chromatography eluting with a 30% ethyl acetate solution in hexane affording 8 as a yellow oil, 22 mg (39% yield). $^1$H NMR (DMSO-d6, ppm): 8.36–8.33 (m, 2 H), 7.77 (s, 1H), 7.41–7.38 (m, 3 H), 7.35–7.31 (d, 1 H), 1.85–1.81 (d, 2H), 1.65–1.55 (m, 4H), 1.48–1.44 (d, 4 H), 1.36 (s, 9H), 1.22 (s, 2H), 0.83 (s, 6H).

EXAMPLE 6

Synthesis of α-phenyl-N-(7-amino-3,5-dimethyladamantane)nitrone (9)

Compound 8 (44 mg) was treated with a 50% trifluroacetic acid solution in dichloromethane. The reaction mixture was stirred at room temperature for 45 min. Solvent was removed in vacuo, and the product was purified by thin layer chromatography eluting with 10% methanol in ethyl acetate affording 9 as a white solid, 32 mg (97% yield). $^1$H NMR (DMSO-d6, ppm): 8.34–8.31 (m, 2 H), 7.84 (s, 1H), 7.49–7.44 (m, 3 H), 7.40–7.38 (dd, 1 H), 1.84–1.80 (d, 2H), 1.66–1.56 (m, 4H), 1.49–1.45 (d, 4 H), 1.22 (s, 2H), 0.83 (s, 6H). MS 298.

The scientific publications, patents or patent applications cited in the various sections of this document are incorporated herein by reference for all purposes.

Equivalents

From the foregoing detailed description of the specific embodiments of the invention, it should be apparent that novel compounds which may be used in the treatment and/or prevention of neurological, inflammatory and/or neuropsychiatric disorders and a unique method of treating said disorders that result from an overproduction of nitric oxide and other free radicals have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular NMDA receptor antagonist, or the particular assay or assessment to gauge the severity or persistence of the neurological, inflammatory or neuropsychiatric disorder is believed to be a matter of routine for a person of ordinary skill in the art with knowledge of the embodiments described herein.

What is claimed is:

1. A compound of the following formula or a pharmaceutically acceptable salt thereof:

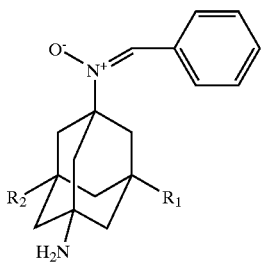

wherein:

$R^1$ and $R^2$ are independently methyl, ethyl, or propyl.

2. A pharmaceutical composition for preventing and/or treating a neurological disorder comprising a therapeutically effective amount of a compound according to claim 1 and a pharmaceutically acceptable carrier.

3. The composition of claim 2, wherein said neurological disorder results from an overproduction of nitric oxide and other free radicals.

4. A pharmaceutical composition for preventing and/or treating an inflammatory disorder comprising a therapeutically effective amount of a compound according to claim 1 and a pharmaceutically acceptable carrier.

5. The composition of claim 4, wherein said inflammatory disorder results from an overproduction of nitric oxide and other free radicals.

6. A method for treating a neurological disorder comprising administering to a patient in need of such treatment a therapeutically effective amount of a compound according to claim 1 and a pharmaceutically acceptable carrier.

7. The method of claim 6, wherein said neurological disorder results from an overproduction of nitric oxide and other free radicals.

8. The method of claim 6, wherein said neurological disorder is selected from the group consisting of hypoxic-ischemic brain injury, trauma, epilepsy, Parkinson's disease, Huntington's disease, amyotrophic lateral sclerosis, and AIDS dementia.

9. A method for treating an inflammatory disorder comprising administering to a patient in need of such treatment a therapeutically effective amount of a compound according to claim 1 and a pharmaceutically acceptable carrier.

10. The method of claim 9, wherein said inflammatory disorder results from an overproduction of nitric oxide and other free radicals.

11. The method of claim 9, wherein said inflammatory disorder is selected from the group consisting of inflammatory bowel disease, rheumatoid arthritis, asthma, atherosclerosis, coronary heart disease and reperfusion injury from heart attack.

12. A method for treating a neuropsychiatric disorder comprising administering to a patient in need of such treatment a therapeutically effective amount of a compound according to claim 1 and a pharmaceutically acceptable carrier.

13. The method of claim 12, wherein said neuropsychiatric disorder is selected from the group consisting of major depression, bipolar disorder, anxiety, drug addiction, drug dependency, drug withdrawal and drug tolerance.

14. A method for preventing the overproduction of nitric oxide and other free radicals in a patient comprising administering to a patient in need of such treatment a therapeutically effective amount of a compound according to claim 1 and a pharmaceutically acceptable carrier.

* * * * *